United States Patent [19]

Kirk

[11] 4,411,067

[45] Oct. 25, 1983

[54] BLADE HOUSING DEVICE FOR CAST CUTTING TOOL

[76] Inventor: Norbert A. Kirk, 43 E. Ohio St., Room 930, Chicago, Ill. 60611

[21] Appl. No.: 294,006

[22] Filed: Aug. 18, 1981

[51] Int. Cl.³ ............................................... B27B 9/02
[52] U.S. Cl. ...................................... 30/124; 30/390; 128/91 A
[58] Field of Search .................. 30/124, 133, 166 R, 30/144, 276, 377, 390, 391; 128/91 A, 317; 144/136 C; 33/169 B, 185 R, 202

[56] References Cited

U.S. PATENT DOCUMENTS

| | | | |
|---|---|---|---|
| 1,546,982 | 7/1925 | Hilthon et al. | 30/390 X |
| 2,070,358 | 2/1937 | Hengstenberg | 30/390 X |
| 2,828,794 | 4/1958 | Damijonaitis | 30/391 X |
| 3,103,069 | 9/1963 | Gary | 30/124 |
| 3,262,471 | 7/1966 | McCarty | 30/391 X |
| 4,022,182 | 5/1977 | Lenkevich | 30/390 |
| 4,241,505 | 12/1980 | Bodycomb et al. | 30/390 |

Primary Examiner—E. R. Kazenske
Assistant Examiner—Douglas D. Watts
Attorney, Agent, or Firm—Larson and Taylor

[57] ABSTRACT

A blade housing device for a cast cutting tool which is used to remove a cast from a patient is disclosed. The housing device includes a housing having a side periphery through which a portion of the edge of the circular saw blade of the cast cutting tool projects varying distances. The housing is attached to the body of the cast cutting tool so that by rotating the cast cutting tool and hence the housing, a different portion of the side periphery can be presented to the cutting area. In this manner, the desired distance of projection of the saw blade, or the desired depth of cut, is easily selected by the user. The housing acts to collect the dust generated by the cutting and the dust can be removed by a suction hose attachable to the front of the housing. For easy blade changing, the housing is pivotally attached relative to the shaft on which the circular saw blade is mounted.

18 Claims, 3 Drawing Figures

BLADE HOUSING DEVICE FOR CAST CUTTING TOOL

FIELD OF THE INVENTION

This invention relates generally to a plaster cast cutting tool and more particularly to a housing device for the circular saw blade of the cast cutting tool which can be rotated along with the tool to determine the depth of the cut.

BACKGROUND OF THE INVENTION

A number of cast cutting tools have been disclosed in the prior art which include means to regulate the depth of a cut of the saw blade. For example, in U.S. Pat. No. 2,374,164 to Castro, a handle assembly containing a saw blade is provided with a substantially rectangular plate or gauge. This plate is eccentrically mounted adjacent the saw blade and bears against the cast as the cast is cut. By rotating the plate, the depth of the cut of the saw blade is determined. Another type of depth regulating device for a cast cutting tool is disclosed in U.S. Pat. Nos. 2,502,656 to Koett and 1,530,023 to Walton. In these patents, the housing for the saw blade is provided with a projecting foot or the like which is adjustable relative to the housing. The foot is designed to ride along the top of the cast being cut so that by adjustment of the foot relative to the housing, the depth of the cut is determined. Still another type of prior art device has a foot which is adjustable relative to the blade housing which rides underneath of the cast. Such devices are disclosed in U.S. Pat. Nos. 2,352,432 to Herrington and 2,221,565 to Bailey. In addition to depth cutting gauges, cast cutting tools have also been provided with complicated dust collection means such as disclosed in U.S. Pat. No. 2,399,677 to Hood et al.

There are a number of disadvantages associated with cast cutting tools such as those discussed above. For example, in each of these cast cutting tools with the exception of the device disclosed in the Castro Patent, the depth of the cut of the saw blade can only be determined by measurement after the adjustment is made. In addition, the hold-down mechanism for the depth regulating foot is subject to coming loose and allowing the blade to cut deeper into the cast and possibly into the patient. Further, the adjustment is not easily and rapidly made. The cutting of casts on inside corners is also not possible with these prior art cutters having depth of cut regulators. Another disadvantage of the prior art devices is that the saw blade can become clogged with the plaster dust. There is also no provision in the prior art devices for a simple and unobtrusive means to collect the plaster dust generated by the saw blade.

SUMMARY OF THE INVENTION

In accordance with the present invention, a blade housing device for a cast cutting tool is provided which regulates the depth of cut of the saw blade and collects the dust generated by the saw blade. The housing device comprises a housing which encloses a substantial portion of the saw blade and a means for attaching the housing to the body of the cast cutting tool. The housing includes a slot through which a portion of the circular saw blade extends varying distances. Thus, when the cast cutting tool and hence the housing are rotated, the depth of cut of the circular saw blade is determined by the portion of the housing in contact with the surface to be cut.

According to a preferred embodiment, the housing is provided with an aperture to which a suction hose is attachable. The portion of the housing through which the circular saw blade extends is curved so that the depth of cut of the circular saw blade is easily changed. Preferably, the body of the cast cutting tool adjacent to the circular blade is curved and the curvature of the housing matches the curvature of the body of the cast cutting tool. In order to clean the dust from inside the housing where it collects, a peripheral side of the housing is pivotable away from the rest of the housing so that the dust is easily emptied therefrom. If desired, indicia indicating the depth of cut of the circular saw blade can be located on the housing. In addition, an external vacuum hose can be positioned adjacent the housing near the shaft. There the shaft extends through the housing, lips internal to the housing can be located about the shaft to retain the plaster dust inside of the housing.

According to another preferred embodiment of the present invention, the housing device includes a hinging means so that the housing is pivotable away from the end of the shaft. With this embodiment, changing of the circular saw blade is accomplished easily.

Other features and advantages of the present invention are stated in or are apparent from the detailed description of presently preferred embodiments of the invention found hereinbelow.

DETAILED DESCRIPTION OF THE PREFERRED EMBODIMENTS

Other embodiments of a housing enclosing a substantial portion of a circular saw blade with the edge of the saw blade projecting varying distances from the housing have also been disclosed in two of applicant's prior U.S. applications, Ser. No. 180,363 filed Aug. 22, 1980 now U.S. Pat. No. 4,316,323 and Ser. No. 260,832 filed May 5, 1981, both of which are entitled "Blade Housing for Cast Cutting Tool". These two prior applications are herein incorporated by reference.

Figure 1:
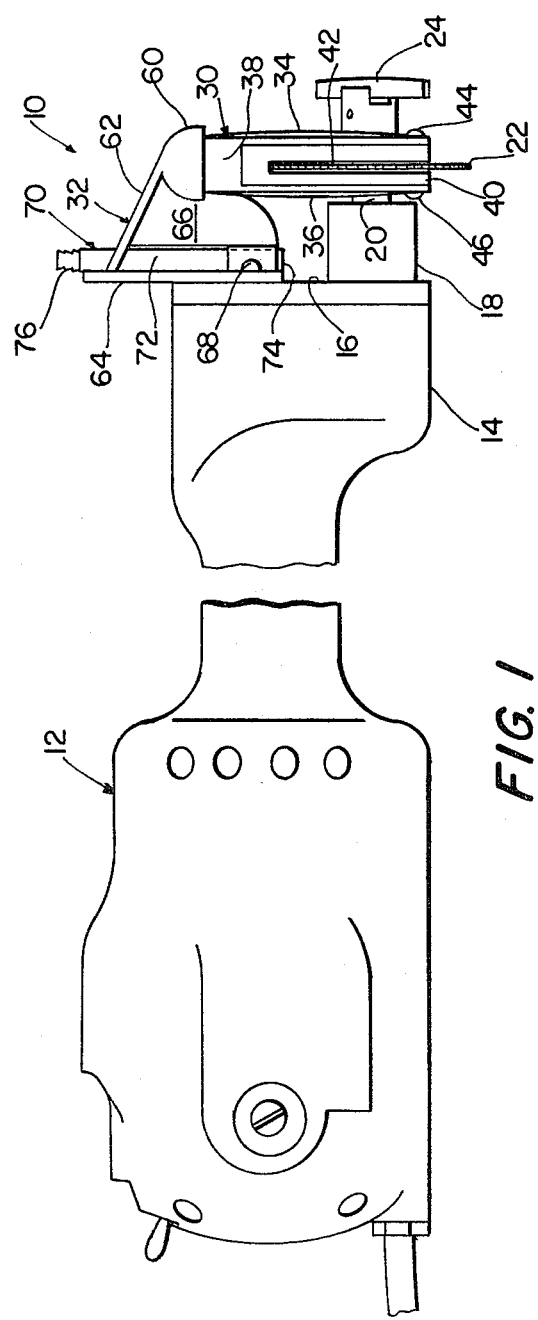
FIG. 1 is a side view of a cast cutting tool with the housing device of the present invention attached thereto.
Figure 2:
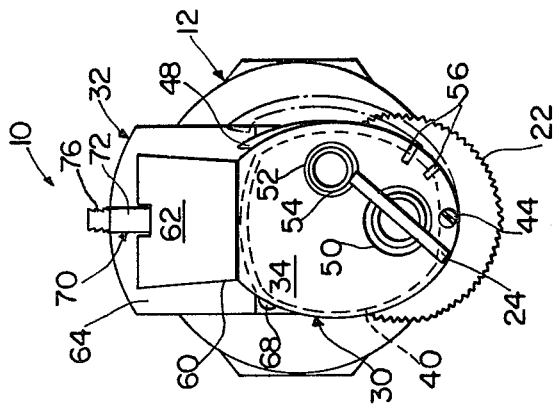
FIG. 2 is a front view of the housing device and cast cutting tool depicted in FIG. 1.

With reference now to the drawings in which like numerals represent like elements throughout the several views, a presently preferred embodiment of the present invention is depicted in FIGS. 1 and 2 and comprises a housing device 10 which is attached to a cast cutting tool 12. Cast cutting tool 12 has a body 14 including a flat front 16 having a generally oval shape. Projecting from the lower end of flat front 16 is an offset neck 18 through which a shaft 20 projects. Shaft 20 is used to mount a circular saw blade 22. Circular saw blade 22 is held on shaft 20 by a butterfly nut 24. As shown in FIGS. 1 and 2, by offsetting shaft 20, a cutting area for saw blade 22 below offset neck 18 remains unobstructed by the remainder of cast cutting tool 12. A suitable cast cutting tool is model 840-20 manufactured by the Stryker Corporation of Kalamazoo, Mich. While this particular model has a saw blade which oscillates, it should be appreciated that the present invention functions in the same manner whether the saw blade oscillates or rotates.

Housing device 10 includes a housing 30 and an attaching means 32 for attaching housing 30 to cast cutting tool 12. Housing 30 is generally oval shaped and includes a front wall 34 and a rear wall 36. Front wall 34 and rear wall 36 are parallel and spaced from one another and are integrally connected by a side wall 38 near the top of housing 30. Side wall 38 mounts front wall 34 and rear wall 36 substantially immovably relative to one another. Enclosing the space between front wall 34 and rear wall 36 below side wall 38 is a side periphery preferably in the form of a ring 40. Ring 40 has an exterior shape which matches the shape of front wall 34 and rear wall 36 up to the point where side wall 38 connects front wall 34 and rear wall 36. A slot 42 is provided in ring 40 through which circular saw blade 22 projects varying distances as best shown in FIG. 2. Ring 40 is attached to front wall 34 by a screw 44 and to rear wall 36 by a screw 46. By aligning screws 44 and 46 coaxial with one another and at the lower portion of front wall 34 and rear wall 36, ring 40 is pivotable from between front wall 34 and rear wall 36. Preferably, ring 40 is frictionally held between front wall 34 and rear wall 36. A tab 48 is provided adjacent side wall 38 which can be easily pulled to pivot ring 40.

An aperture 50 is provided in front wall 34 through which shaft 20 projects. A similar aperture is provided in rear wall 36. Also provided in front wall 34 is an aperture 52 in which a bearing 54 is located. Bearing 54 is adapted to frictionally hold a suction hose inside of the inner ring. Preferably, aperture 52 is located to one side, the left side, of front wall 34 adjacent the side of saw blade 22 which is most frequently the leading cutting edge. Where a suction hose is not used, a suitable plug is fitted in the inner ring of bearing 54. As shown in FIG. 2, indicia 56 are also provided on front wall 34. Indicia 56 are used to provide an indication of the distance of projection, or the depth of cut, of circular saw blade 22 at the position of indicia 56.

Attaching means 32 includes a member 60 which is securely attached to housing 30. Member 60 can be attached to housing 30 in any appropriate manner, such as by gluing, by screws or by being made integral with front wall 34 and rear wall 36. Near the top of member 60 is a cross plate 62 extending back from member 60 to a face plate 64 which is parallel to flat front 16. A reinforcing plate 66 is also provided in a plane perpendicular to cross plate 62 and face plate 64. In this preferred embodiment, member 60, cross plate 62, face plate 64, and reinforcing plate 66 are all integrally formed to produce a rigid attaching means 32. Face plate 64 is securely attached to flat front 16 of cast cutting tool 12 by screws 68 (only one of which is shown) located on either side of reinforcing plate 66. Extending along the front side of face plate 64 and through cross plate 62 and reinforcing plate 66 is a dust collection conduit 70 which in this case is a separate pipe 72. Pipe 72 is frictionally held in place between reinforcing plate 66 and face plate 64 so that the lower end 74 of pipe 72 is adjacent offset neck 18 and shaft 20. Upper end 76 of pipe 72 is adapted to be easily connected to a suitable suction tube.

In order to mount housing device 10 on cast cutting tool 12, butterfly nut 24 is first removed and circular saw blade 22 is pulled off of shaft 20. Circular saw blade 22 is then inserted through slot 42 in ring 40 into housing 30. Housing device 10 is then fitted onto cast cutting tool 10 with shaft 20 extending through housing 30 and circular saw blade 22 contained therein. Butterfly nut 24 is then reattached onto the threaded end of shaft 20 to hold circular saw blade 22 in place. Finally, screws 68 are screwed into flat front 16 of cast cutting cool 12 through face plate 64. This mounts housing device 10 rigidly to cast cutting tool 12 and, as shown in FIG. 2, circular saw blade 22 projects varying distances from housing 30.

In use, cast cutting tool 12 with housing device 10 attached thereto functions in the following manner. Before actuation of cast cutting tool 12, the depth to which saw blade 22 is to cut into the cast is determined. Depending on this depth, cast cutting tool 12 is rotated until the appropriate location of ring 40 is presented to the cutting area. The appropriate location of ring 40 is determined by the distance which saw blade 22 projects from ring 40, which is the distance saw blade 22 will cut into the plaster cast. Once the appropriate location of ring 40 is positioned, which location is evidenced by indicia 56, cast cutting tool 22 is actuated and moved along the direction of the cut to be made. In this manner, a smooth, even and precisely regulated depth of cut is obtained in the cast. If a deeper or shallower depth of cut is desired as cutting progresses, cast cutting tool 10 is easily rotated to position a different portion of ring 40 against the cast to change the depth of cut. It should be appreciated that by exposing a crescent shaped portion of saw blade 2, an inside corner of a plaster cast is easily cut with a portion of the exposed blade.

During the cutting operation, almost all of the plaster dust cut from the cast is trapped between ring 40 and the cast so that most of the dust is deposited in housing 30 by the movement of saw blade 22. Where a source of suction is available, a suction hose is preferably attached to bearing 54 to suck the dust deposited in housing 30 out of housing 30. It should be noted that aperture 52 is offset to one side of housing 30 so as to be somewhat closer to the portion of slot 42 nearest the part of the edge of saw blade 22 which is most frequently used as the cutting edge. Ordinarily, the most frequently used portion of cutting blade 22 is the left side as most right-handed people move cast cutter 10 from right to left, whether cutting toward or away from the body of the patient. By being somewhat closer to the part of the slot nearest the leading edge most frequently used, the suction is greater at this point and the dust created there is more efficiently collected. Of course, suction is applied along the entire length of slot 42 so that no matter which portion of saw blade 22 is used as the leading edge, the dust is collected by the suction through slot 42. Where a source of suction is not available, a plug is inserted in bearing 54 and the dust is allowed to collect in housing 30. After the cutting operation, or after a sufficient amount of dust has collected in housing 30, cast cutting tool is turned off and tab 48 of ring 40 is pulled away from housing 30. This exposes a portion of the interior of ring 40 so that the dust collected in housing 30 can be removed from housing 30 by shaking housing 30. Tab 48 is then pushed back into engagement with side wall 38 of housing 30 and cast cutting tool 10 is again ready for operation. If available, a suction hose can also be attached to upper end 76 of dust collection conduit 70. In this manner, any airborne dust generated by the cutting of circular saw blade 22 is removed from the area of housing 30.

In the preferred embodiment of the present invention depicted in FIGS. 1 and 2, it should be noted that the shape of approximately the lower half of housing 30, when viewed from the front as shown in FIG. 2, is substantially coextensive with the shape of the lower half of body 14 when viewed from the front. By using three matched shapes, body 14 does not interfere with the easy rotation of housing 30 to change the depth of cut of saw blade 22. In fact, where a large flat area of a cast is to be cut, both housing 30 and body 14 can contact the surface to be cut without impairing the easy rotation of housing 30 to change the depth of cut.

Figure 3:
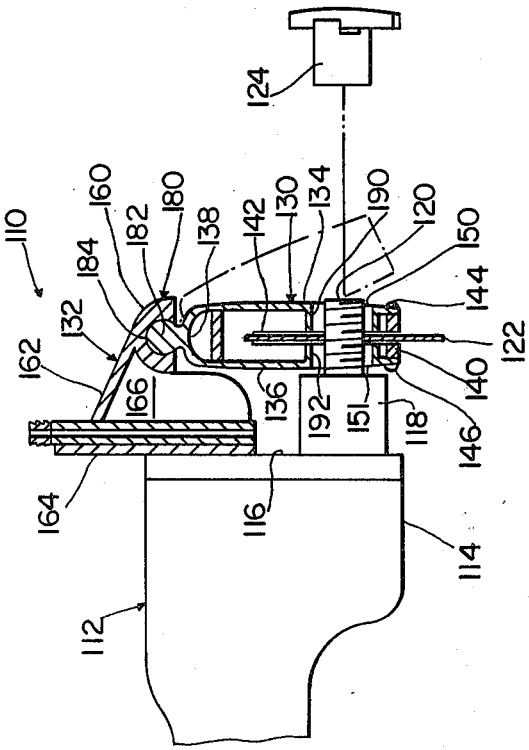
FIG. 3 is a partial cross-sectional side view of an alternative embodiment of the housing device of the present invention attached to a cast cutting tool.

Depicted in FIG. 3 is an alternative embodiment of the present invention which includes a housing device 110 which is similar to housing device 10 depicted in FIGS. 1 and 2. Housing device 110 is mounted on a cast cutting tool 112 having a body 114, a flat front 116, an offset neck 118, a shaft 120, and a circular saw blade 122. Housing device 110 includes a housing 130 with an attaching means 132. Housing 130 includes a front wall 134, a rear wall 136, a side wall 138, and a ring 140 having a slot 142. Ring 140 is mounted between front wall 134 and rear wall 136 by screws 144 and 146. Attaching means 132 includes a member 160, a cross plate 162, a face plate 164, and a reinforcing plate 166.

While housing device 110 is similar to housing device 10, housing device 110 is pivotable away from the end of shaft 120. In order to accomplish this, a hinge means 180 is provided between housing 130 and attaching means 132 so that housing 130 is pivotable beyond the end of shaft 120. Hinge means 180 includes a cylindrical hinge member 182 which is integrally formed with side wall 138 of housing 130. Member 160 of attaching means 132 includes a cylindrical bore 184 in which cylindrical hinge member 182 is received.

Hinge means 180 allows housing 130 to be pivoted to the position shown by the dotted line in FIG. 3 after butterfly nut 124 is removed from the end of shaft 122. In this position, the removal of circular saw blade 122 from housing 130 through a slot 142 and the insertion of a new circular saw blade 122 is easily accomplished without removal of housing device 110 from cast cutting tool 112. After the changing of circular saw blade 122, butterfly nut 124 is reinserted onto the threaded end of shaft 122 to hold circular saw blade 122 in position.

Also depicted in FIG. 3 is an aperture 150 in front wall 134 and an aperture 151 in rear wall 136. Apertures 150 and 151 provide an opening for shaft 120 to extend through housing 130. Extending from front wall 134 toward circular saw blade 122 around aperture 150 is a circular lip 190. A similar circular lip 192 extends from rear wall 136 to the other side of circular saw blade 122 around aperture 151. During operation of cast cutting tool 112, circular lips 190 and 192 act to retain the plaster dust collected in housing 130 within housing 130. Without circular lips 190 and 192, some plaster dust could escape through apertures 150 and 151.

While the present invention has been depicted with housing 30 and 130 having a curved or oval shaped lower end, it would also be possible to provide the lower ends of housing 30 and 130 with a series of straight sides which would approximate the same shape. The series of straight sides could be aligned to correspond to a specific depth of cut as indicated by the indicia shown on housing 30. The outer surface of rings 40 and 140 have also been depicted as being flat. However, as disclosed in applicant's prior U.S. application Ser. No. 260,832, filed on May 5, 1981, a curved outer surface is also possible and would afford the advantage of allowing an easy tipping of housing 30 or 130 relative to the surface to be cut. The tipping of a curved housing reduces the depth of cut as the angle of cut is changed as explained in the above cited application. It should also be appreciated that a number of different hinge means 180 besides that depicted in FIG. 3 are possible to hinge housing 130 relative to attaching means 132. In addition, the location of hinge means 180 can also be changed, for example, to the location where cross plate 162 meets face plate 164.

Thus, while the invention has been described in detail with respect to exemplary embodiments thereof, it will be understood by those of ordinary skill in the art that these and other variations and modifications may be affected in the exemplary embodiments within the scope and spirit of the invention.

I claim:

1. A cast saw device for cutting a cast comprising:
   a cast cutting tool having a body, a shaft extending from said body, and a movable circular saw blade mounted on said shaft;
   a housing device comprising a housing and an attaching means for attaching said housing to said body, said housing enclosing a substantial portion of said saw blade, said housing having a side periphery between front and rear walls thereof and a slot in said side periphery through which a portion of the edge of said saw blade projects varying distances, whereby the depth of cut of said saw blade is determined by the portion of the side periphery which is positioned in contact with the cast; and
   an aperture in said front and rear walls through which said shaft extends and lips extending inwardly from said walls and surround each said aperture to substantially surround said shaft up to said slot whereby the dust collected in said housing is retained therein.

2. A cast saw device as claimed in claim 1 wherein said side periphery in which said slot is located is curved such that inside corners of the cast are easily cut.

3. A cast saw device as claimed in claim 2 wherein said cast cutting tool includes an outer peripheral portion of said body of said cutting tool adjacent said curved side periphery which is substantially coextensive with said curved side periphery.

4. A cast saw device as claimed in claim 1 wherein said housing fully encloses the edge of said saw blade except for the portion extending from said slot so as to retain the plaster dust thrown off of said saw blade inside of said housing and further including an aperture in the front of said housing to which a suction hose is connected whereby the dust collected in said housing is removed through the hose.

5. A case saw device as claimed in claim 1 wherein said housing fully encloses the edge of said saw blade except for the portion extending from said slot so as to retain the plaster dust thrown off of said saw blade inside of said housing and further including a means for pivoting a portion of said side periphery away from the remainder of said housing so as to provide an opening between said housing and the pivoted portion of said side periphery through which the plaster dust collected in said housing is emptied.

6. A cast saw device as claimed in claim 1 wherein said housing device further includes a hinge means for mounting said housing so as to be pivotable beyond the end of said shaft about an axis at right angles to the axis of said shaft and above said shaft.

7. A cast saw device as claimed in claim 2 further including indicia located on the front of said housing adjacent said curved side periphery to indicate the depth of cut of the blade adjacent said indicia.

8. A cast saw device as claimed in claim 1 further including a dust collection conduit having an inlet located adjacent said shaft and outside of said housing and an outlet which is adapted to be attached to a suction hose whereby plaster dust which is not collected in said housing is removed through the suction hose.

9. A cast saw device as claimed in claim 8 wherein said dust collection conduit is held in place by said attaching means.

10. A housing device for the cutting edge of a movable, circular saw blade of a cast cutting tool or the like having a body and a mounting shaft for the blade, comprising:
- a housing comprising a ring, said ring having a slot around a portion of the perimeter of said ring; a front wall attached to the front of said ring and covering the interior of said ring; and a rear wall attached to the rear of said ring and covering the interior of said ring;
- an attaching means for attaching said housing to the body of the cast cutting tool such that said housing surrounds the circular saw blade and such that the saw blade projects varying distances beyond said ring through said slot and whereby the depth of cut of the saw blade is determined by the portion of said ring which is positioned in contact with a surface to be cut; and
- a securing means for securing said front wall immovable with respect to said rear wall, and wherein said ring is pivotally attached to said front wall and said rear wall such that said ring is pivotable from between said front wall and said rear wall so as to uncover a portion of the interior of said ring whereby dust is easily removed from the interior of said ring.

11. A housing device as claimed in claim 10 wherein said ring is oval shaped such that inside corners of the surface are easily cut.

12. A housing device as claimed in claim 10 wherein said front wall and said rear wall have peripheral portions which are substantially coextensive with the portion of said ring having said slot.

13. A housing device as claimed in claim 10 wherein said front wall includes an aperture to which a suction hose is connectable to remove dust collected in said housing.

14. A housing device as claimed in claim 10 wherein said ring includes an outwardly directed tab extending beyond said front and said rear walls.

15. A housing device as claimed in claim 10 further including a hinge means located between said housing and said attaching means for mounting said housing pivotable beyond the end of the shaft of the cast cutting tool about an axis at right angles to the axis of the shaft and above the shaft.

16. A housing device as claimed in claim 10 further including a dust collection conduit having an outlet which is adapted to be attached to a suction hose and an inlet located adjacent the shaft and outside of said housing whereby dust not collected in said housing is removed.

17. A housing device as claimed in claim 10 further including an aperture in said rear wall and said front wall through which the shaft extends, and a circular lip extending inwardly around the shaft from both said rear wall and said front wall adjacent to the saw blade whereby the dust collected in said housing is retained therein.

18. A housing device as claimed in claim 13 wherein said aperture is located to one side of said housing so as to be adjacent to the portion of said saw blade which is most frequently used as the leading edge.

* * * * *